US005856587A

United States Patent [19]

Visca et al.

[11] Patent Number: 5,856,587

[45] Date of Patent: Jan. 5, 1999

[54] FLAME EXTINGUISHING COMPOSITIONS

[75] Inventors: Mario Visca, Alessandria; Gianfranco Spataro, Lissone; Giuseppe Marchionni, Milan, all of Italy

[73] Assignee: Ausimot SpA, Milan, Italy

[21] Appl. No.: 812,964

[22] Filed: Mar. 5, 1997

[30] Foreign Application Priority Data

Mar. 7, 1996 [IT] Italy .................................. MI9600443

[51] Int. Cl.$^6$ .............................. C07C 43/12; A62D 1/00

[52] U.S. Cl. .............................. 568/677; 568/683; 252/2; 252/8; 169/46; 169/47

[58] Field of Search ............................ 169/46, 47; 252/2, 252/8; 568/677, 683

[56] References Cited

U.S. PATENT DOCUMENTS

| | | | |
|---|---|---|---|
| 4,954,271 | 9/1990 | Green | 252/8 |
| 5,132,455 | 7/1992 | Lagow | 568/683 |
| 5,476,974 | 12/1995 | Moore et al. | 528/271 |
| 5,484,546 | 1/1996 | Minor et al. | 252/8 |
| 5,502,094 | 3/1996 | Moore et al. | 524/145 |
| 5,567,765 | 10/1996 | Moore et al. | 524/801 |
| 5,605,882 | 2/1997 | Klug et al. | 252/67 |

FOREIGN PATENT DOCUMENTS

| | | |
|---|---|---|
| 0695755A | 2/1996 | European Pat. Off. . |
| 9004675 | 5/1990 | WIPO . |
| 9324586 | 12/1993 | WIPO . |
| 9426837 | 11/1994 | WIPO . |
| 9526218 | 10/1995 | WIPO . |
| 9532174 | 11/1995 | WIPO . |
| 9640371 | 12/1996 | WIPO . |
| 9640834 | 12/1996 | WIPO . |

*Primary Examiner*—Peter A. Szekely
*Attorney, Agent, or Firm*—Nikaido Marmelstein Murray & Oram, LLP

[57] ABSTRACT

Extinguishing compositions comprising a liquid extinguishing agent constituted by hydrofluoropolyethers having general formula $$HF_2CO(CF_2O)_n(CF_2CF_2O)_mCF_2H$$

wherein n and m are integers comprised between 0 and 20, excluding when m and m are contemporaneously 0 and having boiling point between 30° and 200° C. and having an O/C molar ratio between 0.5–1.

8 Claims, No Drawings

FLAME EXTINGUISHING COMPOSITIONS

The present invention refers to flame-extinguishing compositions which are not objectable as to toxicity, have no impact on ozone and have low impact on global warming, having drop-in characteristics, i.e. suitable to be utilized in normal plants and flooding automatic systems in place of the extinguishing compositions at present used without having to proceed to change the existing plants, or suitable to be utilized in portable systems such as extinguishers.

The technical problem to be solved by the present invention concerns the need to have available extinguishing compositions which are not toxic and have the characteristics above mentioned. Such problem is particularly felt since the laws of various countries have banned or are about to ban the use of most extinguishing compositions, utilized up to now, owing to impact problems on ozone.

As examples of compositions which cannot be utilized any longer due to their impact on ozone and on which most flooding automatic plants are dimensioned, we can mention those based on fluorocarbons containing bromine such as Halon 1301.

The banning of Halons for the damage of the ozone layer due to the presence of bromine in the molecule has made necessary the study of new systems capable of assuring the flame extinction, both for total flooding systems and for portable systems such as extinguishers.

Various extinguishers have been proposed and are present in the recent patent literature, such as perfluorocarbons (PFC), for instance perfluoropropane (PFC 218) and its higher homologues, hydrofluorocarbons (HFC) such as pentafluoroethane (HFC 125), heptafluoropropane (HFC 227) and hexafluoropropane (HFC 236), HFC mixtures and chlorohydrofluorocarbons (HCFC) such as NAF® III, marketed by Safety-Hi-tech.

See in particular patent U.S. Pat. No. 4,954,271 covering NAF® III, wherein extinguishing compositions are described, which comprise:

a) a HCFC selected from 11 (trichlorofluoromethane), 123 (2,2-dichloro, 1,1,1-trifluoroethane), 123b (1,2-dichloro2,2-difluoroethane), optionally in the presence of a component b) selected from HCFC among which 12 (dichlorodifluoromethane), 114 (1,2-dichlorotetrafluoroethane), 22 (chlorodifluoromethane), 124 (2 chloro-1,1,1,2-tetrafluoroethane), and HFC among which 125 (pentafluoroethane), 134a (1,2,2,2-tetrafluoroethane), and c) a detoxifying agent selected from terpenes and unsaturated acids.

Patent EP 439479 can also be mentioned, which describes as flame-extinguishing agents compounds having the general formula $C_xH_yF_z$ wherein x=3, y=1 or 2, z=6 or 7 to be utilized in fire extinguishing concentrations, optionally in admixture with acidity scavengers and other compounds with extinguishing effect. The acidity scavenger agents are the detoxifying agents indicated above.

From the analysis of the experimental data of EP '479 it can be noticed that the best results are obtained when hydrogen is not present as end group but is inside the chain as one can see from the difference between 227 ($CF_3CHFCF_3$) and 236 ($CF_3CHFCF_2H$).

Extinguishing compositions have been unexpectedly and surprisingly found which comprise a liquid extinguishing agent consisting essentially of hydrofluoropolyethers having the general formula $$HF_2CO(CF_2O)_n(CF_2CF_2O)_mCF_2H$$

wherein n and m are integers comprised between 0 and 20, excluding when m and n are contemporaneously 0 and having boiling point between 30° and 200° C. and preferably between 60° and 150° C., and having an O/C molar ratio between 0.5–1.

Hydrofluoropolyethers are generally mixtures of components having a different molecular weight with boiling points comprised in the ranges previously described.

Such extinguishing compositions comprise at least HFPE and a propellant.

As propellants, inert gases among which nitrogen or helium, or preferably hydrofluorocarbons having extinguishing properties, alone or in admixture with each other and/or with inert gases indicated above, can be utilized.

The inert gas has the function to warrant when necessary the pressure sufficient for the flowing out of the product from the nozzles of the extinguishing equipment.

In particular as propellants having specific extinguishing power it can be cited hydrochlorofluorocarbons having three carbon atoms ($HCFC_3$), and preferably hydrofluorocarbons having three carbon atoms ($HFC_3$) with a boiling temperature lower than 0° C. or their mixtures. Among these hydrofluorocarbons (HCF) pentafluoroethane (HCF 125), heptafluoropropane (HFC 227) and hexafluoropropane (HFC 236) can be preferably mentioned. It has been found that with the extinguishing composition of the present invention the concentration of the propellant or the amount of HFC utilized in the flame-extinguishing process is lower than that necessary for the propellant utilized alone to extinguish the flame. This means that the global efficiency of flame-extinguishing of the compositions of the invention is equal to or higher than that obtainable with the HFC described in the art mentioned above.

In particular the combination of the hydrofluoropolyether (HFPE) propellants having extinguishing power (e.g. pentafluoroethane (HFC 125), heptafluoropropane (HFC 227) and hexafluoropropane (HFC 236) and hydrofluorocarbon/hydrochlorofluorocarbon HFC/HCFC blend, as f.i. NAF® III), and it is absolutely unexpected, allows to extinguish the fire by using a lower amount of the extinguishing compositions of the present invention with respect to the extinguishiung agents of the prior art alone.

The advantages in utilizing the hydrofluoropolyethers of the present invention, without binding to any theoric functioning mechanism of the flame-extinction, are the following:

- improved extinguishing efficiency due to the contribution of the liquid phase with high molecular weight,
- lower toxicity and reduction of the potential risks bound to the presence of high concentrations of gaseous substances,
- protective/extinguishing effect due to the deposit of a small fraction of inert liquid on the surfaces potentially involved by fire. The low surface tension of the liquid allows the penetration of the same inside surfaces having even a complex configuration,
- cleaning of the system. The liquid component optionally deposited on surfaces to be protected is inert and quickly evaporates as endowed with low evaporation heat,
- absence of chlorine and bromine atoms in the molecule,
- low potential of greenhouse effect,
- ODP effect equal to zero.

The concentration of the hydrofluoropolyether of the present invention is that necessary to extinguish fire in particular the concentration is generally comprised between 5–50%, preferably 5–15% v/v.

The results of the present invention are more unexpected if we consider that tests carried out by the Applicant have shown that perfluoropolyethers having perfluoroalkylic terminals —$CF_3$, —$C_2F_5$, —$C_3F_7$ and also fluoropolyethers containing only one end hydrogen have extinguishing properties industrially insufficient.

The combination of end groups, the structure of end groups —$OCF_2H$, the particular O/C ratio has unexpectedly allowed and, contrary to what one could infer from the art, to identify a specific category of compounds with high extinguishing properties.

The above mentioned detoxifying agents of the art can be also utilized in the compositions of the invention, to neutralize the toxic fumes due to the decomposition of the extinguishing agents, in particular HF.

See patents U.S. Pat. No. 4,954,271 or patent WO 95/26218, incorporated herein by reference.

The compositions of the invention can be utilized in the extinguishing systems at present known, whether they are for instance fixed extinguishing systems such as total flooding or portable systems such as extinguishers, etc.

Hydrofluoropolyethers of the present invention are obtained by means of decarboxylation processes of alkaline salts obtained by hydrolysis and salification of the corresponding acylfluorides, by means of processes known in the art. For instance decarboxylation is carried out in the presence of hydrogen-donor compounds, for instance water, at temperatures of 140°–170° C. and under pressure of at least 4 atm. See for instance patent EP 695775 and the examples reported therein.

The following examples are given for illustrative purposes but are not limitative of the scope of the invention.

EXAMPLE 1

(operating conditions)

In a circular aluminium tray having a surface of 572 $cm^2$ water was introduced up to ⅓ of the tray capacity (about 500 ml).

Heptane was added in an amount at least sufficient to give an uniform layer of inflammable liquid on the surface of the water (10–30 ml).

After 5 sec. from the ignition of heptane one proceeded to the flame extinction by utilizing the composition of the invention, contained in 180 net g aerosol cans at room temperature and at the autogenous pressure of the propellant.

The extinction time and the amount of extinguishing product utilized as an average of 3 measures, were measured.

EXAMPLE 1

(comparative)

With the modalities described above, a can containing pure HFC 125 was utilized. To extinguish flame, 8 seconds were necessary with an employment of 12 g of extinguishing agent.

EXAMPLE 2

Example 1 was repeated by utilizing a can containing a mixture consisting of 90% by weight of HFC 125 and 10% by weight of HFPE having the structure $$HCF_2O(CF_2O)_n(CF_2CF_2O)_mCF_2H$$

and boiling temperature comprised between 80° and 110° C.

The products is constituted by a HFPE mixture with different molecular weight with number average $M_n$ 325 and O/C ratio equal to 0.56.

The flame was extinguished in 5 sec. with the employment of 9 g of extinguishing mixture.

EXAMPLE 3

Example 1 was repeated by utilizing a mixture comprising 70% by weight of HFC 125 and 30% by weight of HFPE of Example 2.

The extinction of the flame required 4 sec. and 6 g of extinguishing mixture.

EXAMPLE 4

(comparative)

Example 3 was repeated by utilizing a mixture constituted by 70% by weight of HFC 125 and 30% by weight of a monofunctional HFPE having O/C ratio equal to 0.27 and number average molecular weight 320. Such HFPE had the general formula $$F(C_3F_6O)_p(CF_2O)_qCF_2H$$

and in the case of the utilized sample, p was 1 or 2 and q was zero.

The extinguishing agent values are: extinction time 8 sec., amount of extinguishing mixture 9 g.

We claim:

1. Extinguishing compositions comprising a liquid extinguishing agent constituted by hydrofluoropolyethers having the formula $$HF_2CO(CF_2O)_n(CF_2CF_2O)_mCF_2H$$

wherein n and m are integers comprised between 0 and 20, excluding when m and n are contemporaneously 0 and having a boiling point between 30° and 200° C., and having an O/C molar ration between 0.5–1 and further comprising a propellant.

2. Extinguishing compositions comprising a liquid extinguishing agent according to claim 1 having a boiling point between 60° and 150° C.

3. Extinguishing compositions according to claim 1 wherein the propellant is selected from the group consisting of an inert gas selected from the group consisting of nitrogen and helium and hydrofluorocarbons, hydrochlorofluorocarbons with exinguishing properties alone and in admixture with each other and/or with said inert gas.

4. Extinguishing compositions according to claim 4 wherein the hydrofluorocarbon with extinguishing properties utilized as propellant is selected from hydroflourocarbon (HFC) with a boiling temperature lower than 0° C.

5. Extinguishing compositions according to claim 4 wherein the hydrofluorocarbon is selected from the group consisting of: pentafluoroethane (HFC 125), heptafluoropropane (HFC 227) and hexafluoropropane (HFC 236).

6. Extinguishing compositions according to claim 1, wherein the detoxifying agent is selected from the group consisting of terpenes and unsaturated acids and mixtures thereof.

7. A method for extinguishing a fire comprising contacting said fire with a composition comprising:

hydrofluoropolyethers having the formula $HF_2CO(CF_2O)_n(CF_2CF_2O)_mCF_2H$ wherein n and m are integers comprised between 0 and 20, excluding when m and n are contemporaneously 0 and having a boiling point between 30° and 200° C. and having an O/C molar ratio between 0.5–1.

8. Extinguishing compositions comprising a liquid extinguishing agent constituted by hydrofluoropolyethers having the formula $$HF_2CO(CF_2O)_n(CF_2CF_2O)_mCF_2H$$

wherein n and m are integers comprised between 0 and 20, excluding when m and n are contemporaneously 0 and having a boiling point between 30° and 200° C., and having an O/C molar ration between 0.5–1 and further comprising a detoxifying agent.

* * * * *

UNITED STATES PATENT AND TRADEMARK OFFICE

CERTIFICATE OF CORRECTION

PATENT NO. : 5,856,587

DATED : January 5, 1999

INVENTOR(S) : Visca et al.

It is certified that error appears in the above-identified patent and that said Letters Patent is hereby corrected as shown below:

On the title page,
Item [73], delete "Ausimot SpA" insert therefor

-- Ausimont S.p.A. --

Signed and Sealed this

Eighth Day of June, 1999

Attest:

Q. TODD DICKINSON

Attesting Officer

*Acting Commissioner of Patents and Trademarks*